United States Patent [19]

Chan et al.

[11] Patent Number: 5,468,499
[45] Date of Patent: Nov. 21, 1995

[54] LIPOSOMES CONTAINING THE SALT OF PHOSPHORAMIDE MUSTARD AND RELATED COMPOUNDS

[75] Inventors: Kenneth K. Chan, Dublin; Aeumporn Srigritsanapol, Columbus, both of Ohio

[73] Assignee: Ohio State University, Columbus, Ohio

[21] Appl. No.: 152,493

[22] Filed: Nov. 15, 1993

[51] Int. Cl.$^6$ ............................. A61K 37/22; A61K 9/52
[52] U.S. Cl. ........................... 424/450; 514/883; 558/199
[58] Field of Search ........................... 424/450; 514/883; 588/180

[56] References Cited

U.S. PATENT DOCUMENTS

| | | | |
|---|---|---|---|
| 4,186,183 | 1/1980 | Steck et al. | 424/450 |
| 4,753,788 | 6/1988 | Gamble | 424/450 |
| 4,841,085 | 6/1989 | Farquhar et al. | 538/180 |
| 4,873,088 | 10/1989 | Mayhew et al. | 424/450 |
| 4,920,016 | 4/1990 | Allen et al. | 424/450 |
| 4,963,367 | 10/1990 | Ecanow | 424/455 |
| 5,013,556 | 5/1991 | Woodle et al. | 424/450 |
| 5,047,245 | 9/1991 | Bally et al. | 424/450 |
| 5,077,056 | 12/1991 | Bally et al. | 424/450 |
| 5,077,057 | 12/1991 | Szoka | 424/450 |
| 5,091,552 | 2/1992 | Farquhar | 558/180 |
| 5,190,929 | 3/1993 | Borch et al. | 514/80 |
| 5,306,727 | 4/1994 | Borch et al. | 514/398 |

*Primary Examiner*—Ronald W. Griffin
*Attorney, Agent, or Firm*—Calfee Halter & Griswold

[57] ABSTRACT

The present invention provides an anti cancer treatment which has an improved stability and does not produce acrolein. The invention includes dichlorodiethyl phosphoramide drugs including, for example, the cyclohexylamine salt phosphoramide mustard and isophosphoramide mustard and mixtures thereof, which have been entrapped by liposomes. Preferably the liposomes contain sphingomyelin and cholesterol.

9 Claims, 7 Drawing Sheets

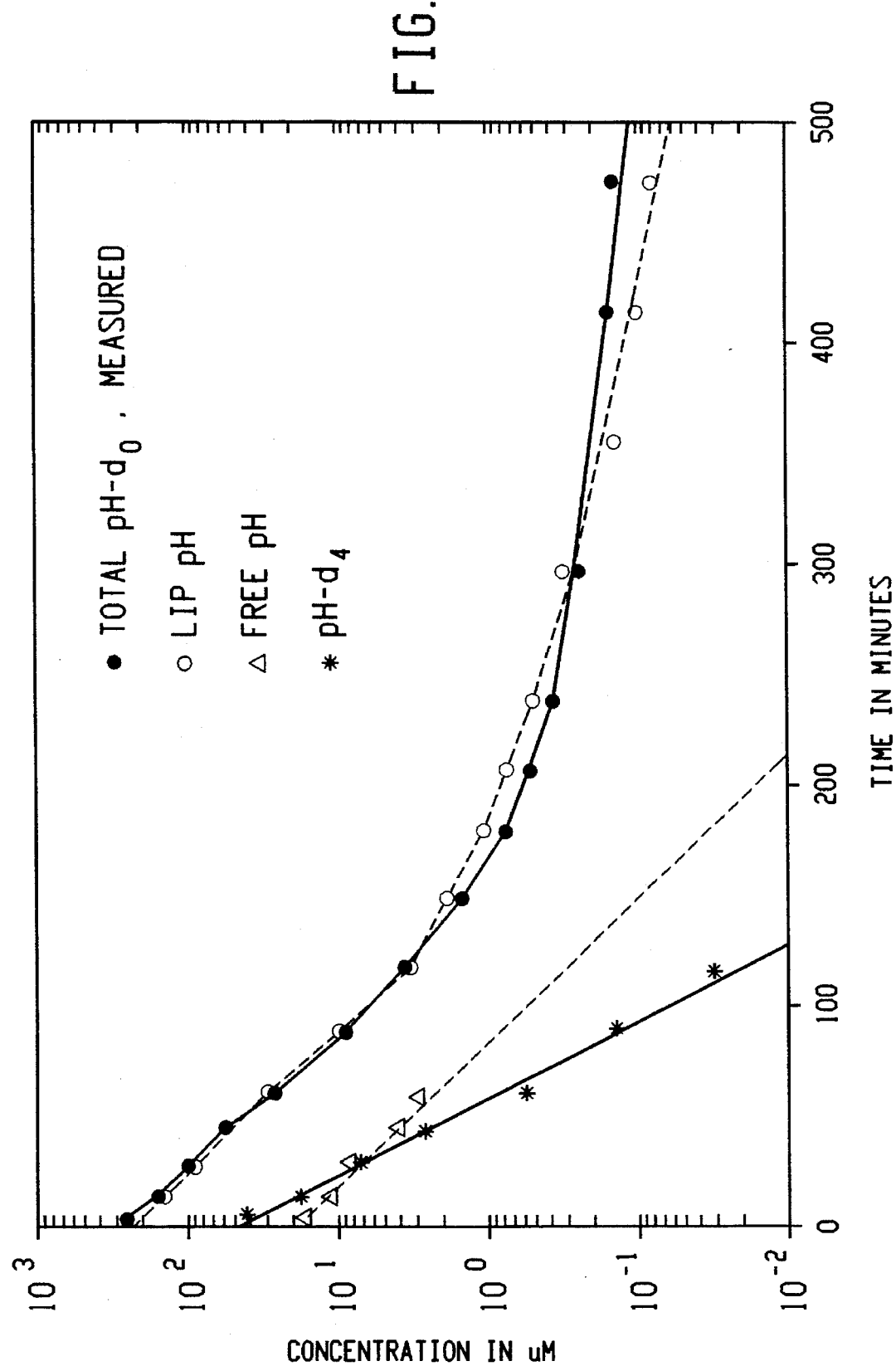

LIPOSOMES CONTAINING THE SALT OF PHOSPHORAMIDE MUSTARD AND RELATED COMPOUNDS

BACKGROUND OF THE INVENTION

Cyclophosphamide is an established anti-cancer drug discovered in the 1950's, see Arnold, H. and Bourseaux, F., "Synthese Und Abbau Cytostatisch Wirksanfer Cyclischer N-Phosphamidester Des Bis-(β-Chlorathyl)amins," *Angewandte Chemie.*, 70, 539, 541 (1958). Cyclophosphamide is a common anti-cancer treatment which is now used to treat a variety of tumors in over 6 million people annually.

A related drug, the cyclohexylamine salt of phosphoramide mustard, was evaluated as a treatment for cancer in the 1960's. However, the clinical trials failed to show anti-tumor effect. See Nathanson, L., Hall, T. C., Rutenberg, A., and Shadduck, R. K., "Clinical Toxicologic Study of Cyclohexylamine Salt of N, N-bis(2-Chlorethyl) Phosphorodiamidic Acid (NSC-69945; OMF-59)," *Cancer Chemother Rept.*, 51(1):35–39, (1967). Accordingly, phosphoramide mustard salt was abandoned as a treatment for cancer.

It was subsequently discovered that cyclophosphamide is not directly tumoricidal; instead the metabolites of cyclophosphamide exert the tumoricidal properties. Cyclophosphamide is metabolized via the hepatic crosomal oxidation to form the primary metabolite 4-OHCP/ALdp, 4-hydroxycyclophosphamide aldophosphamide. Subsequently chemical or enzymatic S-elimination generates two metabolites phosphoramide mustard, the acid form of the salt that was administered in clinical trials in the 1960's, and acrolein. It was also determined that the phosphoramide mustard has the greatest anti-tumor effect of the cyclophosphamide metabolites. In contrast, the acrolein produces the most side effects.

It would be desirable to have a highly active anti-tumor agent which when metabolized does not produce acrolein, yet is stable.

SUMMARY OF THE INVENTION

The present invention provides an anti cancer treatment which has an improved stability and does not produce acrolein. The invention includes dichlorodiethyl phosphoramide drugs including, for example, the cyclohexylamine salt of phosphoramide mustard and isophosphoramide mustard and mixtures thereof, which have been entrapped by liposomes. Preferably the liposomes contain sphingomyelin and cholesterol.

BRIEF DESCRIPTION OF THE DRAWINGS

FIG. 7 shows a typical concentration profile of free phosphoramide mustard and liposome entrapped, salt of phosphoramide mustard in rat plasma from 0–500 minutes.

DETAILED DESCRIPTION OF THE INVENTION

Figure 1:
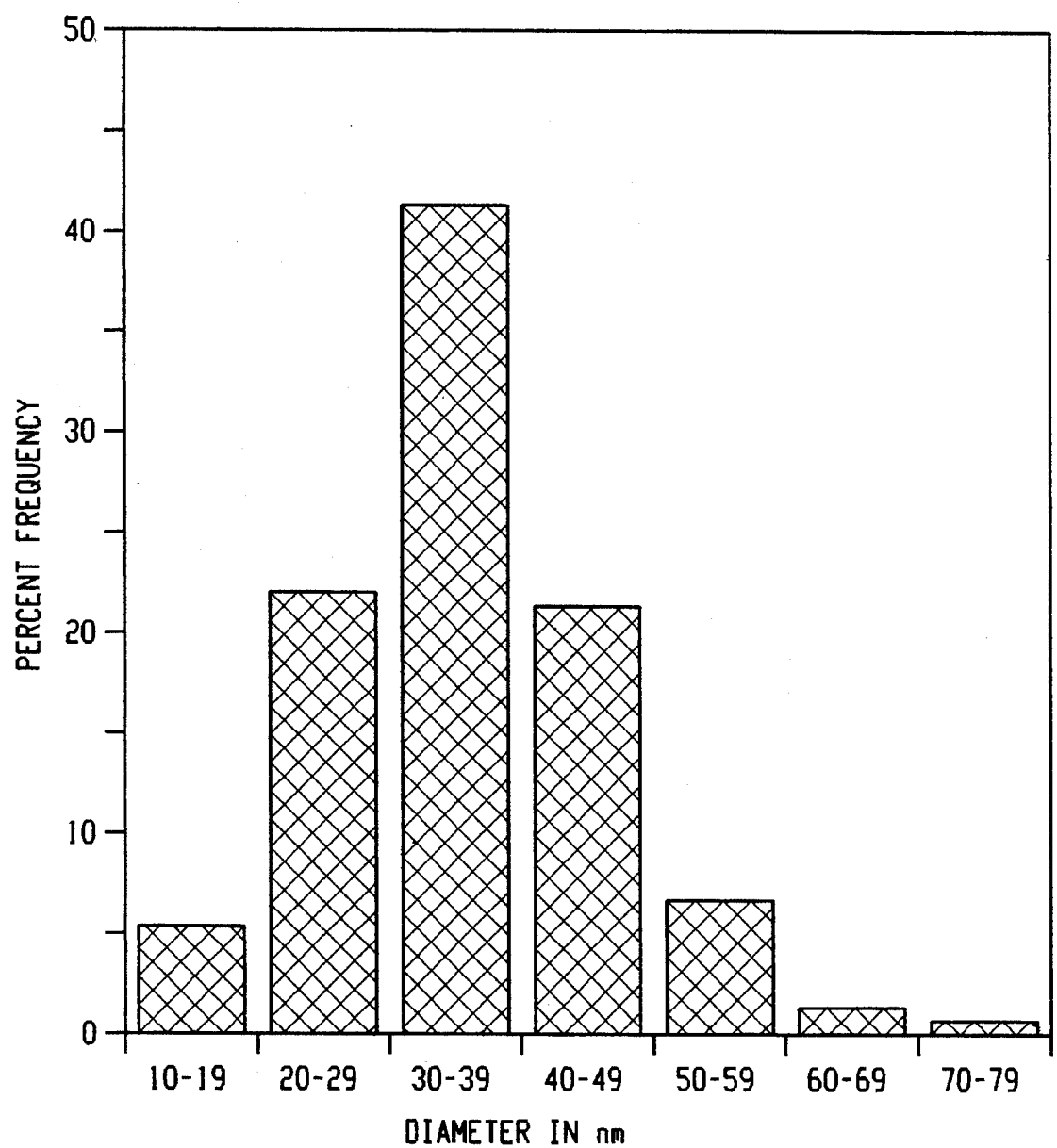
FIG. 1 is a graph showing the size distribution of the liposomes produced herein.
Figure 2:
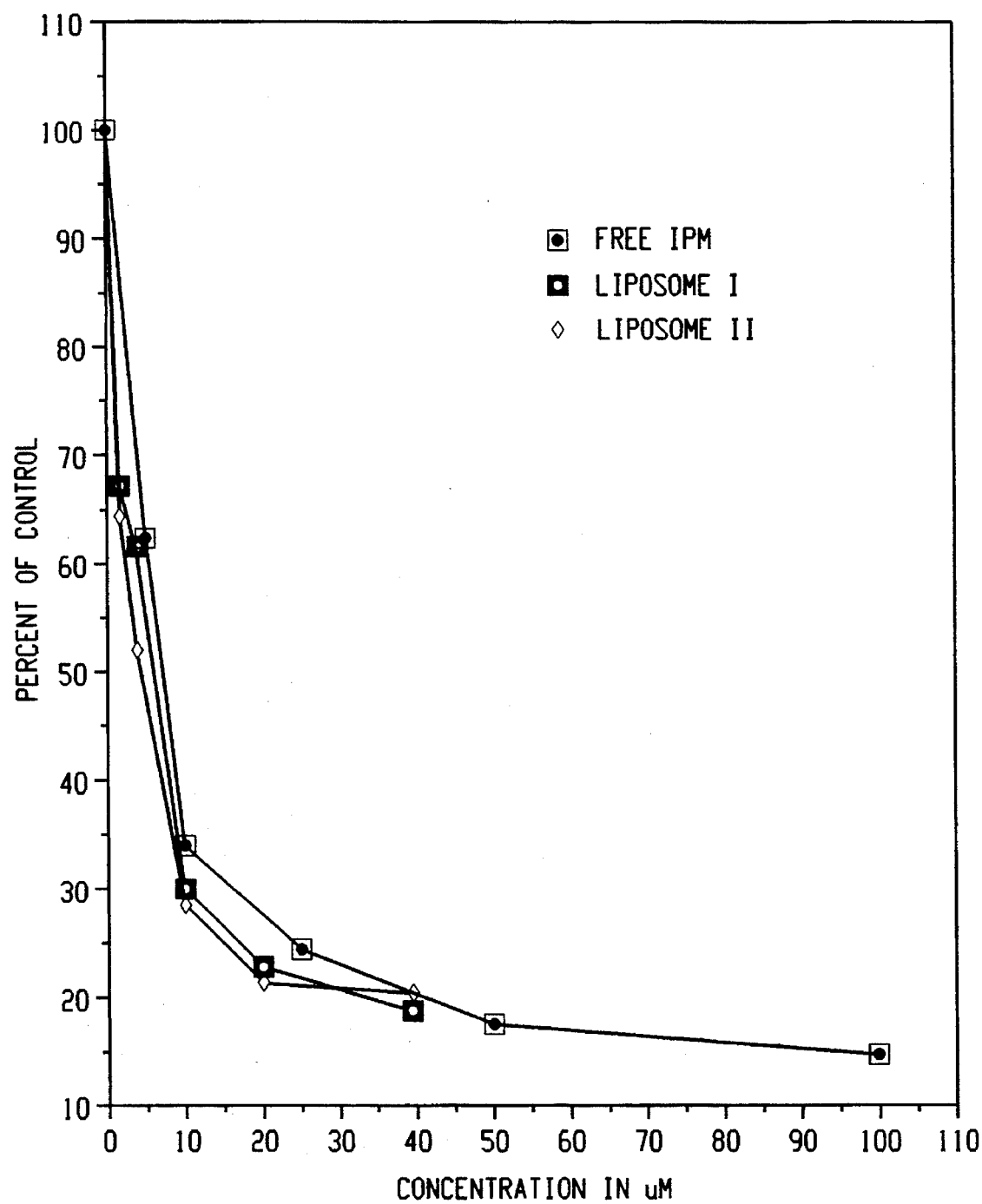
FIG. 2 is a graph showing the cytotoxicity of isophosphoramide mustard on L1210 leukemia cells after 72 hours.

The present invention provides an anti-cancer treatment which has an improved stability and does not produce acrolein. The invention relates to dichloroethyl phosphoramide drugs including for example the cyclohexylamine salt of phosphoramide mustard hereinafter also referred to as the "salt of phosphoramide mustard", isophosphoramide mustard, and mixtures thereof, which have been entrapped by liposomes. Preferably the liposomes are composed of sphingomyelin and cholesterol. As used herein, entrapped includes being enclosed within as well as being associated with the liposomes.

Phosphoramide mustard is an alkylating agent at physiologic temperatures and pH, and appears to alkylate DNA directly via an aziridinium intermediate compound to produce interstrand cross-linking DNA in the tumor cell. The isophosphoramide mustard acts in a similar manner. Isophosphoramide mustard, an isomer of phosphoramide mustard is an anti-cancer drug. Struck, R. F., Dykes, D. J., et al. "Isophosphoramide Mustard a Metabolite of Isophosphoramide with Activity Against Murine Tumors Comparable to Cyclophosphamide," *Br. J Cancer,* Vol 47, p. 15 (1983). The isophosphoramide mustard is quite water-soluble and more unstable in aqueous solutions than the phosphoramide mustard. Due to its polar nature, the isophosphoramide mustard is not readily taken up by cells.

The salt of phosphoramide mustard which is entrapped in the liposomes has the following structure:

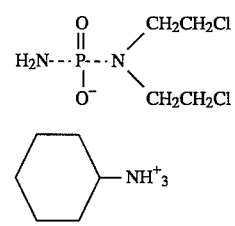

It can be obtained from the National Cancer Institute, or it may be synthesized according to the method disclosed in Friedman, O. M., and Seligman, A. M., "Preparation of N-Phosphorylated Derivatives of Bis-β-Chloroethylamine," *J. Amer. Chem. Soc.,* 76, 655–658, 1954.

Once in the body, the salt of phosphoramide mustard forms the phosphoramide mustard which has the following structure:

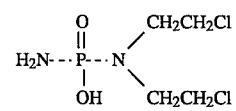

Isophosphoramide mustard has the following structure:

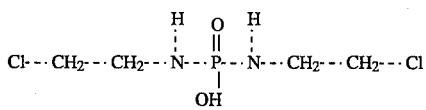

Isophosphoramide mustard can be obtained from the National Cancer Institute or it can be synthesized according to the method disclosed in Struck, R. F., Dykes, D. J., et al. "Isophosphoramide Mustard a Metabolite of Ifosfamide with Activity Against Murine Tumors Comparable to Cyclophosphamide," *Br. J. Cancer*, Vol 47, p 15 (1983).

Preparation of Liposomes

Example 1

The cyclohexylamine salt of phosphoramide mustard was incorporated into the aqueous compartment of small unilamellar vesicles (SUV) composed of sphingomyelin and cholesterol in a 1:1 mole ratio. Specifically, Bovine brain sphingomyelin, 88 mg, from Avanti Chemical Company having a MW of 731.12, and 46.4 mg cholesterol, from Signa Chemical Company at the molar ratio of 1:1 were dissolved in 1 ml of 2:1 (vol/vol) chloroform and methanol in a 13×100 mm pyrex test tube. The organic solvent was evaporated to dryness under a stream of nitrogen leaving a thin lipid film around the tube. The dried thin lipid film was placed in a vacuum chamber to remove the trace amount of the organic solvent. Next, 88 mg of the cyclohexylamine salt of phosphoramide mustard was dissolved in 1 ml of pH 7.4, 0.067M sodium phosphate buffer in 0.9% sodium chloride and the resultant phosphoramide mustard solution was added to the tube containing the thin lipid film. Multilamellar vesicles (MLV) were formed when the tube was vigorously shaken and bath-sonicated in cold temperature (about 0° C.) water for about 20 minutes. The MLV suspension was extruded back and forth for 11 passes through two polycarbonate membranes of 100 nm pore size employing the "Liposofast®" extrusion apparatus from Avestin in Ottawa, Canada. The Liposofast® apparatus was assembled and used according to the manufacturer's instructions. The purpose of repeated extrusion was to resize vesicles and rearrange lipid bilayers in order to make SUV of homogeneous size. The in situ repeated extrusion of MLV through two polycarbonate membranes of defined pore sizes such as 100 nm produced homogeneous vesicles. The average diameter of vesicles was determined by the pore sizes of the polycarbonate membrane used for extrusion. The size of liposomes can also be controlled by changing the pore sizes of the polycarbonate membrane. At the end of the extrusion, the liposome-drug suspension turns from opaque to a transparent, clear solution. The resulting suspension is composed of some of the salt of phosphoramide mustard entrapped in liposomes, as well as some of the salt of phosphoramide mustard not entrapped in liposomes.

Example 2

To prepare the liposomes containing isophosphoramide mustard, an isophosphoramide mustard solution was prepared by dissolving 88.0 mg of isophosphoramide mustard in 1 ml of 0.067M, pH 7.4 sodium phosphate buffer solution. The liposome isophosphoramide mustard suspension was made as in Example 1 except the isophosphoramide mustard solution is added to the lipid film rather than the phosphoramide mustard solution.

Example 3

Liposomes containing the salt of phosphoramide mustard were prepared as in Example 1, except a 2 to 1 ratio of sphingomyelin to cholesterol was used.

Separation of Liposomes From Free Drug

Ten 3 c.c. disposable syringe barrels, employed as columns, were plugged with polyethylene frits and filled with sephadex G-50, which had been swollen in phosphate buffer overnight. The columns were placed in a 16×100mm test tube and centrifuged at 180 X g for 1 minute to remove the excess water. The column was placed into a new 16×100 mm test tube. A 100 µl of either the liposome-isophosphoramide mustard/suspension or the liposome salt of phosphoramide mustard suspension were added drop by drop to the top of the column.

Next, 500 µl of cold phosphate buffer was added, drop by drop, to the columns and the columns were centrifuged at 180 X g for 1 minute. The liposomes were collected and pooled. This method separates liposomes from the drug that is not entrapped in liposomes.

The entrapment efficiency was determined either by subtracting the free drug obtained during the separation procedure from the total drug added in initially making the liposomes or by disrupting the liposomes and quantifying the drug directly. The average entrapping efficiency was 5.7±0.9% (SD, n=8).

Negative stained electron micrographs confirmed the formation of liposomes and revealed that they were small and unilamellar with an average diameter of 33±2.4 nm (SD, n=256). The size distribution is shown in FIG. 1.

Preparation of Blank Liposomes

To prepare the blank liposomes, that is, liposomes not containing any drug which were used as controls, 46.4 mg of cholesterol and 88.0 mg of sphingomyelin were placed into a 13×100 mm Pyrex test tube and liposomes were prepared as in Example 1, except one ml of 0.067M, pH 7.4 sodium phosphate buffer solution was added then and sonicated at room temperature. The resulting liposomes were passed through the Liposofast® extruder fitted with two polycarbonate membranes having a pore size of 100 nm. The process was repeated five and a half cycles.

Evaluation Of Liposomes Containing Phosphoramide Mustard or Isophosphoramide Mustard The stability of liposomes was evaluated in phosphate buffered saline, culture media, and fresh rat plasma. The amount of salt of phosphoramide that leaked from the liposomes was determined during 8 hours using gas chromatography/mass spectrography. The results are shown in Table 1.

TABLE 1

Stability of Liposomes Containing the Salt of Phosphoramide Mustard

| Liposome comp. | Drug | Temp. | PBS | Media | Plasma | % PM remaining after 8 hours |
|---|---|---|---|---|---|---|
| SM/CH 1:1 | PM | 4° C. | X | | | 100% |
| 1:1 | PM | 37° C. | X | | | 77% |
| 1:1 | PM | 37° C. | | X | | 81% |
| 1:1 | PM | 37° C. | | | X | 40% |

| no liposomes | Drug | Temp. | PBS | Media | Plasma | Half-life (minutes) |
|---|---|---|---|---|---|---|
| no liposomes | PM | 37° C. | X | | | ≤10 |
| no liposomes | PM | 37° C. | | X | | ≅26 |
| no liposomes | PM | 37° C. | | | X | ≅60 |

PBS - phosphate buffered saline
PM - the salt of phosphoramide mustard

The stability evaluations of the liposomes of Example 3, which were composed of sphingomyelin and cholesterol in a 2 to 1 ratio, indicated that they were not as stable as the liposomes of Example 1, which contained a 1 to 1 ratio of sphingomyelin to cholesterol. Accordingly, the liposomes of Example 3 are less preferred.

As can be seen from Table 1, the enclosure of the salt of phosphoramide mustard in liposomes, significantly increases the stability of the salt of phosphoramide mustard which has a half life of 10 minutes in rat plasma.

In Vitro Evaluation

To evaluate the cytotoxicity of free isophosphoramide mustard to murine leukemic L1210 cells, 9 ml of cell suspension containing $3\times10^6$ cells was placed in each of six 15-ml-centrifuge tubes. Appropriate amount of stock isophosphoramide mustard solutions, lacking liposomes, were added to each tube to produce final drug concentrations of 0 (no drug), 5, 10, 25, 50, and 100 µM. The isophosphoramide mustard solution and cell suspension were mixed by shaking. Two millimeter aliquots were removed and added to 24-well culture plates. To evaluate the cytotoxicity of liposomes containing isophosphoramide mustard, 60 ml of the cell suspension containing $3\times10^6$ cells was prepared. Nine ml of cell suspension was placed in each of six 15-ml-centrifuge tubes. Appropriate amounts of liposome-entrapped isophosphoramide mustard were added to each tube to produce final drug concentrations of 0 (no drug), 2, 4, 10, 20, and 40 µM. Appropriate amounts of blank liposomes were added to maintain constant amount of liposomes in each well. The contents were mixed by shaking. Two milliliter aliquots were removed and added to 24-well plates. Triplicate cultures were prepared of each drug concentration.

The cultures were placed into the incubator containing 5% carbon dioxide at 37° C. for 72 hours after which they were counted.

The cytotoxicity data for free isophosphoramide mustard on the murine leukemic L1210 cells are shown in Table 2. The cytotoxicity is expressed as the number of cells grown following 72 hours exposure to different concentrations of the isophosphoramide mustard solution. The control cells were not exposed to any isophosphoramide mustard. The percentage of cell-kill for drug treated cells relative to those of the control is shown in FIG. 1.

The cytotoxicity data for liposomes containing isophosphoramide mustard on leukemic L1210 cells is shown in Tables 3 and 4. The cytotoxicity is expressed as the number of cells grown following 72 hours exposure to different concentrations of liposome-entrapped isophosphoramide mustard. The control was exposed to 0 µM concentration of liposome-entrapped isophosphoramide mustard, but included blank liposomes.

TABLE 2

Free Isophosphoramide Mustard Cytotoxicity to L1210 Cells After 72 Hours Exposure

| IPM (µM) | read 1 | read 2 | read 3 | average | cell #/ml | % of control |
|---|---|---|---|---|---|---|
| 100 | 3023 | 2933 | 3048 | 3001 | 128720 | 0.1508 |
|  | 3878 | 3855 | 3664 | 3799 | | |
|  | 2807 | 2826 | 2928 | 2854 | | |
| 50 | 3546 | 3594 | 3655 | 3598 | 149320 | 0.1750 |
|  | 3703 | 3707 | 3705 | 3705 | | |
|  | 3940 | 3932 | 3815 | 3896 | | |
| 25 | 5438 | 5233 | 5364 | 5345 | 212609 | 0.2491 |
|  | 5082 | 4989 | 5164 | 5078 | | |
|  | 5521 | 5479 | 5567 | 5522 | | |
| 10 | 7176 | 7100 | 7139 | 7138 | 289422 | 0.3391 |
|  | 7061 | 7203 | 6920 | 7061 | | |
|  | 7514 | 7417 | 7590 | 7507 | | |
| 5 | 13486 | 13608 | 13332 | 13475 | 535133 | 0.6270 |
|  | 12760 | 12995 | 13135 | 12963 | | |
|  | 13949 | 13682 | 13558 | 13696 | | |
| 0 | 22172 | 22184 | 2284 | 22213 | 853458 | 1.0000 |
|  | 20634 | 20737 | 21100 | 20824 | | |
|  | 21088 | 20853 | 20976 | 20972 | | |

IPM Isophosphoramide

As shown in Table 2, the control which received no isophosphoramide mustard had the highest cell growth. As the concentration of the isophosphoramide mustard increased, the cell concentration decreased.

TABLE 3

Liposome Entrapped Isophosphoramide Mustard Cytotoxicity to L1210 Cells After 72 Hours Exposure (Study I)

| IPM (µM) | read 1 | read 2 | read 3 | average | cell #/ml | % of control |
|---|---|---|---|---|---|---|
| 40 | 4596 | 4481 | 4501 | 4526 | 173369 | 0.1943 |
|  | 4143 | 4136 | 4212 | 4164 | | |
|  | 4367 | 5319 | 4253 | 5313 | | |
| 20 | 5232 | 5308 | 5261 | 5267 | 203631 | 0.2283 |
|  | 4930 | 5135 | 5018 | 5028 | | |
|  | 4970 | 4990 | 4973 | 4978 | | |
| 10 | 6870 | 6847 | 6962 | 6893 | 270196 | 0.3029 |
|  | 6652 | 6547 | 6620 | 6606 | | |
|  | 6808 | 6713 | 6775 | 6765 | | |
| 4 | 11491 | 11866 | 11729 | 11695 | 553187 | 0.6201 |
|  | 10966 | 33398 | 11358 | 18574 | | |
|  | 11287 | 11262 | 11110 | 11220 | | |
| 2 | 15612 | 15758 | 15793 | 15721 | 606631 | 0.6800 |
|  | 14790 | 15083 | 15008 | 14960 | | |
|  | 14796 | 14787 | 14865 | 14816 | | |
| 0 | 23902 | 24188 | 24222 | 24104 | 892093 | 1.0000 |
|  | 22601 | 22349 | 22660 | 22537 | | |
|  | 20090 | 20364 | 20345 | 20266 | | |

IPM - isophosphoramide mustard

TABLE 4

Liposome Entrapped Isophosphoramide Mustard Cytotoxicity to L1210 Cells After 72 Hours Exposure (Study II)

| IPM (μM) | read 1 | read 2 | read 3 | average | cell #/ml | % of control |
|---|---|---|---|---|---|---|
| 40 | 5188 | 5216 | 5224 | 5209 | 197333 | 0.0264 |
|  | 4631 | 4828 | 5072 | 4844 |  |  |
|  | 4815 | 4658 | 4768 | 4747 |  |  |
| 20 | 5528 | 5585 | 5475 | 5529 | 209809 | 0.2194 |
|  | 5149 | 5299 | 5093 | 5180 |  |  |
|  | 5205 | 4859 | 5014 | 5026 |  |  |
| 10 | 7195 | 7267 | 7296 | 7253 | 278502 | 0.2912 |
|  | 6762 | 6617 | 6676 | 6685 |  |  |
|  | 6872 | 6987 | 6991 | 6950 |  |  |
| 4 | 12921 | 13385 | 13193 | 13166 | 500409 | 0.5233 |
|  | 12226 | 12449 | 12287 | 12321 |  |  |
|  | 12100 | 11915 | 12116 | 12044 |  |  |
| 2 | 16093 | 16057 | 16183 | 16111 | 619262 | 0.6476 |
|  | 14946 | 15125 | 15023 | 15031 |  |  |
|  | 15192 | 15376 | 15339 | 15032 |  |  |
| 0 | 28942 | 28929 | 29122 | 28998 | 956302 | 1.0000 |
|  | 23496 | 23486 | 23293 | 23425 |  |  |
|  | 19417 | 19057 | 19426 | 19300 |  |  |

IPM Isophosphoramide

As shown in Table 3 and 4, the cell growth for the two studies with the liposome entrapped isophosphoramide mustard are similar. The control cells which received only blank liposomes exhibited the highest cell growth; the cell growth decreased as the concentration of the liposome-entrapped isophosphoramide mustard increased. When cells were exposed to the highest concentration of isophosphoramide mustard, 40 μM, the cells displayed the lowest cell growth.

Figure 3:
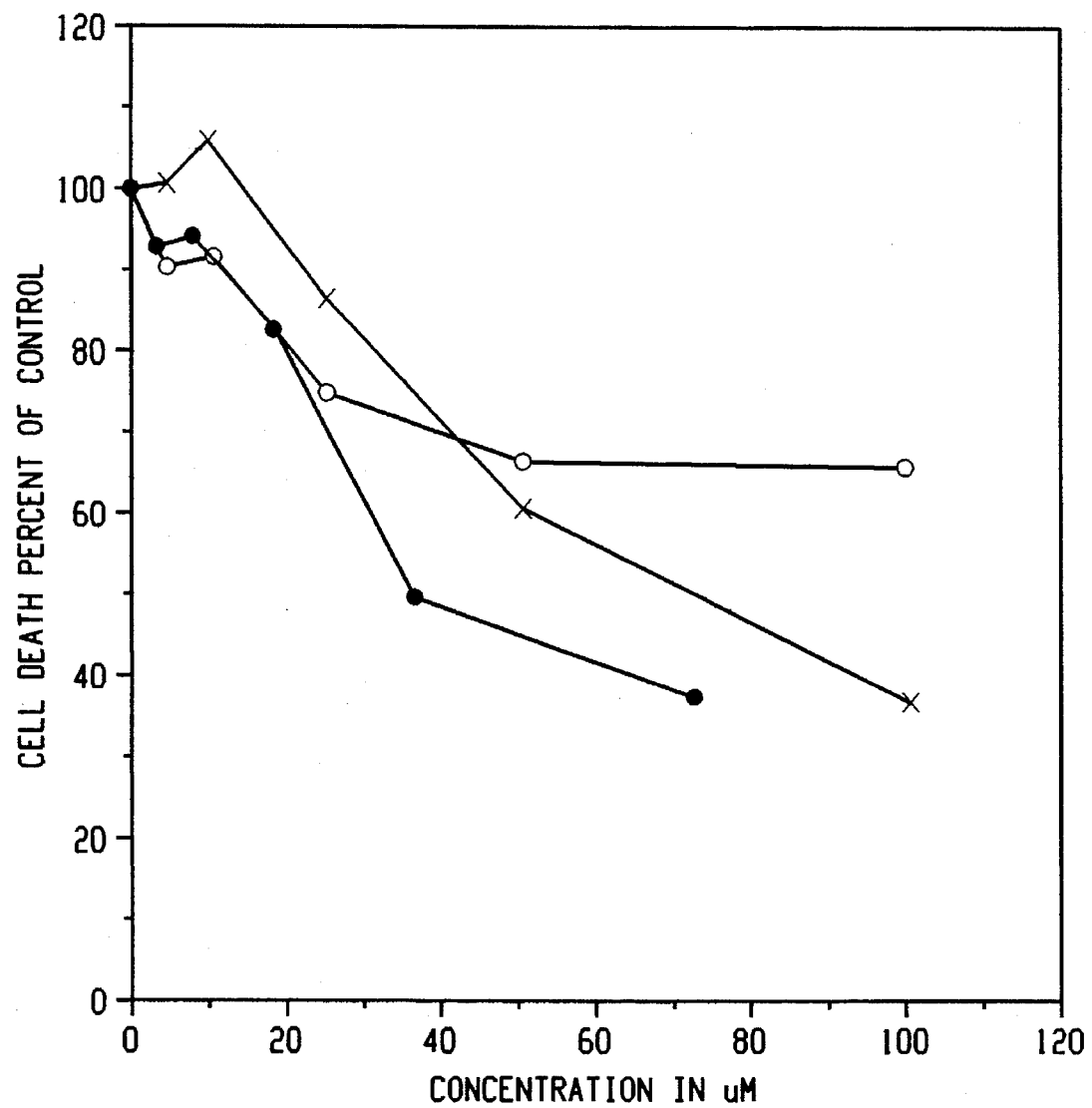
FIG. 3 is a graph showing the cytotoxicity of phosphoramide mustard on L1210 leukemia cells after 2 hours.

The cytotoxicity of the free isophosphoramide mustard and the cytotoxicity of liposome-entrapped isophosphoramide mustard are compared in FIG. 3. The vertical axis represents the percentage of cell death relative to the control cells, while the horizontal axis represents the concentration isophosphoramide mustard, whether liposome-entrapped or free. The liposome-entrapped isophosphoramide mustard is more effective at killing the leukemia cells than the free isophosphoramide mustard, especially at the lower concentrations.

In Vitro Evaluation of the Salt of Phosphoramide Mustard

Figure 4:
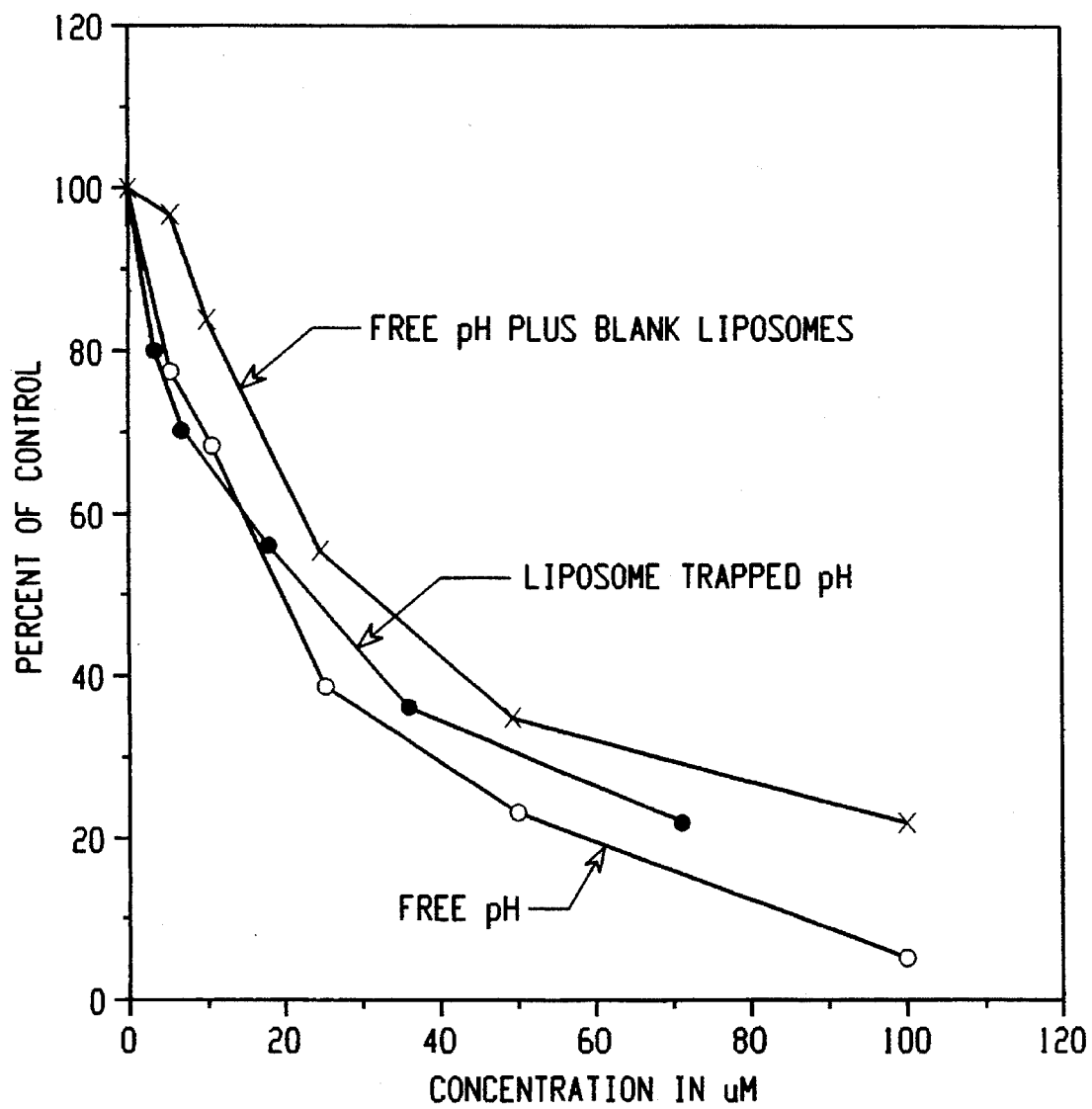
FIG. 4 is a graph showing the cytotoxicity of phosphoramide mustard on L1210 leukemia cells after 3.5 hours.
Figure 5:
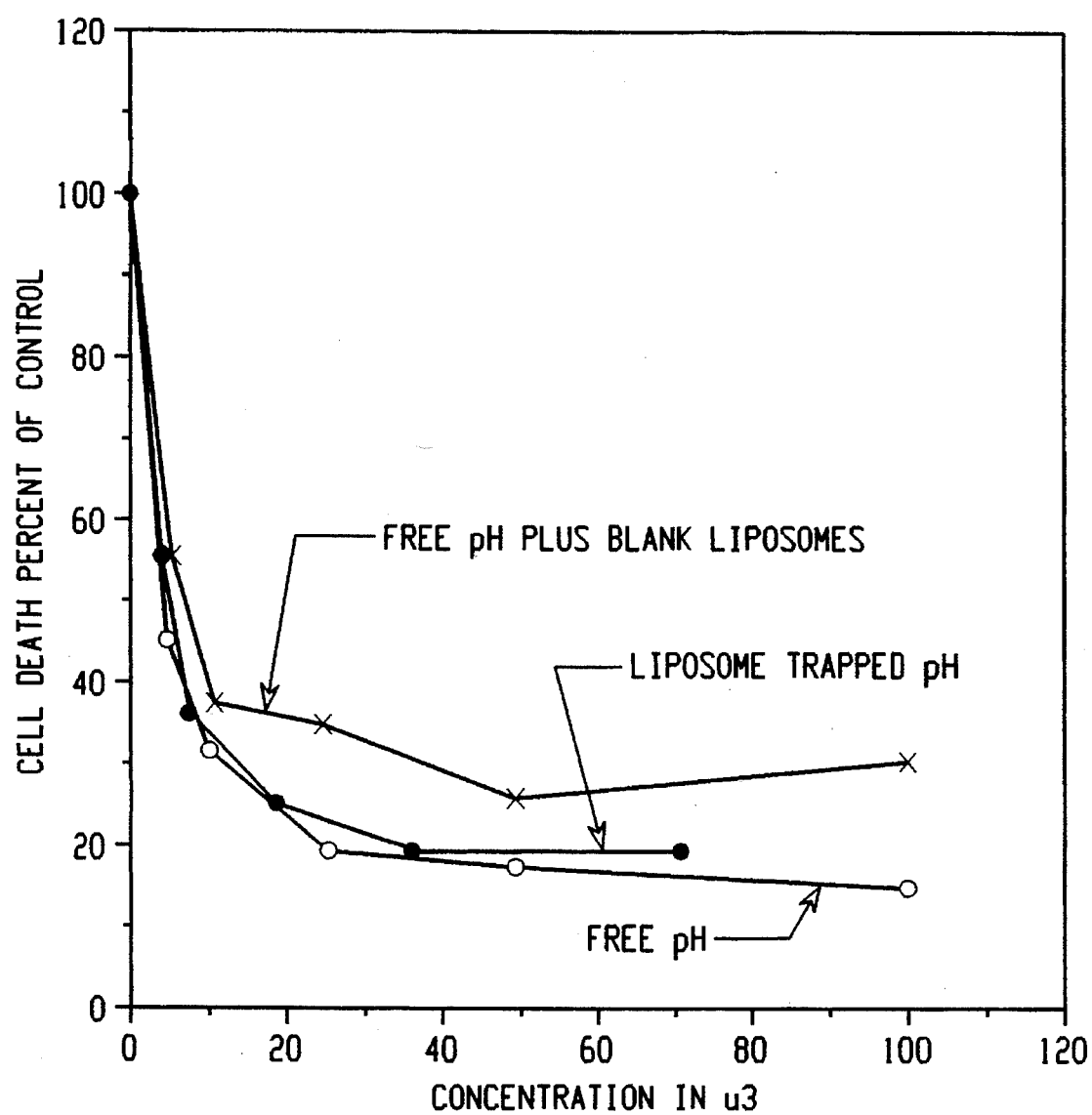
FIG. 5 is a graph showing the cytotoxicity of the salt of phosphoramide mustard on L1210 leukemia cells after 72 hours.

The salt of phosphoramide mustard entrapped in liposomes composed of sphingomyelin and cholesterol, in a 1:1 mole ratio made according to Example 1 was tested for its cytotoxicity against murine leukemia L1210 cells following 2, 3.5, and 72 hour exposure times. The culture methods were the same as described above with the isophosphoramide mustard. The results for the 2 hour exposure is shown in FIG. 3, the results for the 3.5 exposure is shown in FIG. 4 and Table 5, and the results for the 72 hour exposure is shown in FIG. 5 and Table 6.

TABLE 5

Cytotoxicity of the Salt of Phosphoramide Mustard Entrapped in Liposomes as Compared to the Free Salt of Phosphoramide Mustard After 3.5 Hours Exposure

| | Liposomal PM | | | Free PM | | Free PM/ empty liposomes | |
|---|---|---|---|---|---|---|---|
| PM (μM) | #cells per ml[a] | % of Control (SD) | PM (μM) | #cells per ml[a] | % of Control (SD) | #cells per ml[a] | % of Control (SD) |
| 0 | 460,520 | 100 | 0 | 453,324 | 100 | 401,684 | 100 |
| 3.6 | 393,213 | 85.38 (2.7) | 5 | 376,769 | 83.11 (3.2) | 396,622 | 98.74 (2.3) |
| 7.2 | 355,382 | 77.17 (3.0) | 10 | 342,911 | 75.64 (1.9) | 354,516 | 88.26 (1.8) |
| 18 | 303,338 | 65.87 (1.7) | 25 | 231,916 | 51.16 (1.7) | 261,996 | 65.22 (1.2) |
| 36 | 226,707 | 49.23 (1.6) | 50 | 175,916 | 38.81 (1.6) | 193,858 | 48.26 (1.4) |
| 72 | 173,591 | 37.69 (1.2) | 100 | 107,053 | 23.62 (0.9) | 151,138 | 37.63 (2.1) |

[a]average #cells per ml obtained from a triplicate determination, each determination was an average of three readings.

TABLE 6

Cytotoxicity of the Salt of Phosphoramide Mustard Entrapped in Liposomes as Compared to the Free Salt of Phosphoramide mustard after 72 Hours Exposure

| | Liposomes Containing PM | | | Free PM | | Free PM/with empty liposomes | |
|---|---|---|---|---|---|---|---|
| PM ($\mu$M) | #cells per ml[a] | % of Control (SD) | PM ($\mu$M) | #cells per ml[a] | % of Control (SD) | #cells per ml[a] | % of Control (SD) |
| 0 | 679,822 | 100 | 0 | 695,862 | 100 | 530,156 | 100 |
| 3.6 | 371,382 | 54.63 (3.4) | 5 | 305,884 | 43.96 (4.9) | 284,604 | 53.68 (2.3) |
| 7.2 | 236,773 | 34.83 (1.4) | 10 | 212,858 | 30.59 (2.4) | 191,560 | 36.13 (0.7) |
| 18 | 164,849 | 24.25 (0.9) | 25 | 134,436 | 19.32 (0.6) | 178,862 | 33.74 (1.6) |
| 36 | 125,667 | 18.49 (1.6) | 50 | 115,529 | 16.60 (0.3) | 131,378 | 24.78 (0.1) |
| 72 | 124,591 | 18.33 (1.9) | 100 | 101,573 | 14.60 (0.8) | 152,547 | 28.77 (1.2) |

[a]average #cells per ml obtained from a triplicate determination, each determination was an average of three readings.
PM - salt of phosphoramide mustard As shown in FIG. 3, after two hours the liposomes containing the salt of phosphoramide mustard showed enhanced cytotoxic effect as compared to either free salt of phosphoramide mustard or to free salt of phosphoramide mustard in the presence of empty liposomes. Increased cytotoxicity was found after 3.5 hours and 72 hours exposure to liposomes containing the salt of phosphoramide mustard. Free phosphoramide mustard at 3.5 and 72 hour exposures also displayed increased cytotoxicity. The increased cytotoxicity at 18 $\mu$m and above of the salt of the phosphoramide mustard in the liposomes appears to be due to the entrapment of the salt of the phosphoramide mustard and not due to any synergistic effect between salt of free phosphoramide mustard and liposomes since the salt of free phosphoramide mustard/empty liposome formulation produced a slight decrease in cytotoxicity as compared to the cytotoxicity of the liposome containing the salt of phosphoramide mustard.

In Vivo Evaluation of Phosphoramide Mustard

Figure 6:
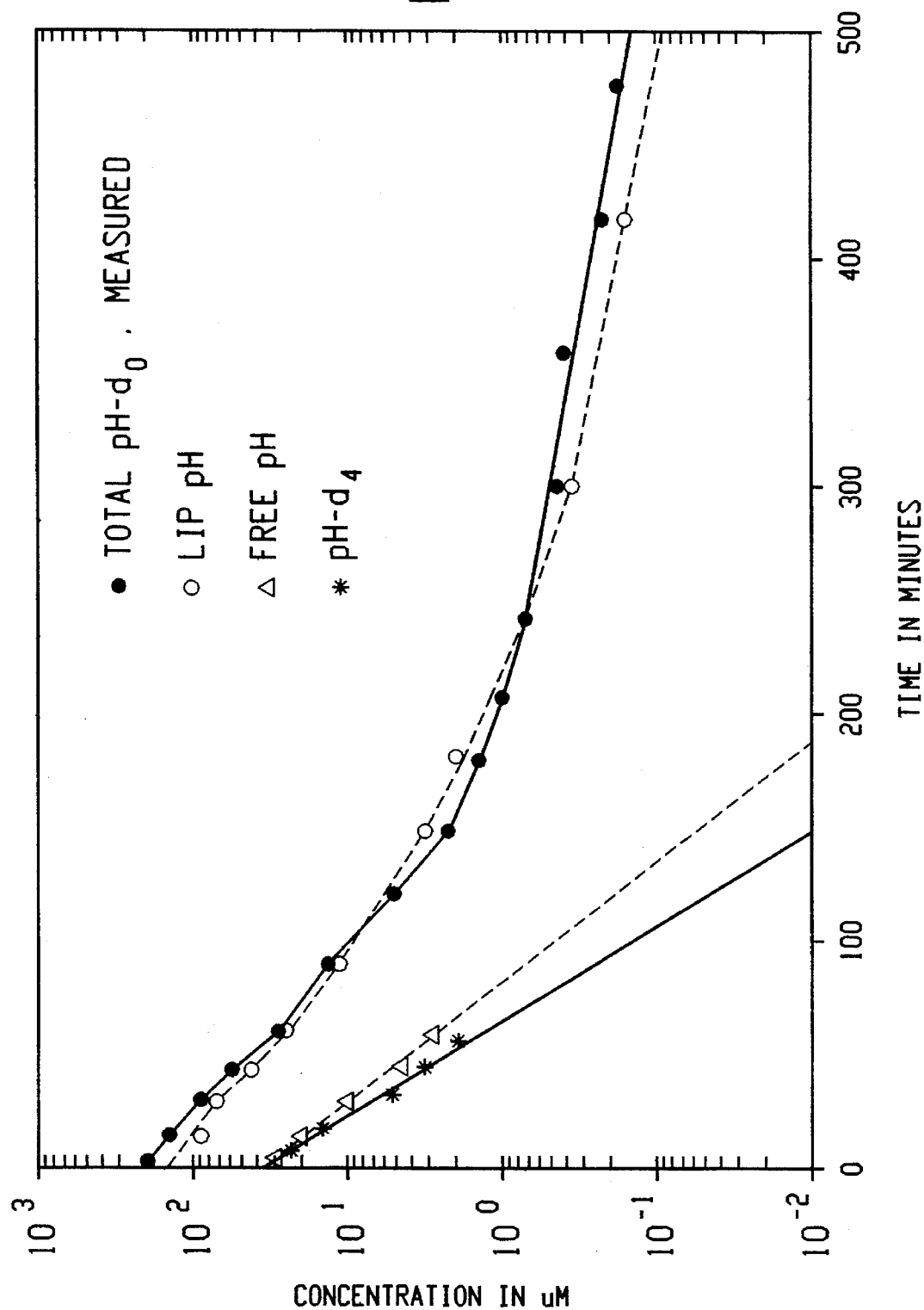
FIG. 6 shows a typical concentration profile of free phosphoramide mustard and liposome entrapped, salt of phosphoramide mustard in rat plasma from 0–500 minutes.

The pharmacokinetics of the salt of phosphoramide mustard entrapped in the liposomes of Example 1 were studied and compared with the pharmacokinetics of the salt of the free phosphoramide mustard and phosphoramide mustard derived from the parent drug cyclophosphamide. Male Sprague-Dawley rats received liposomes containing the salt of phosphoramide mustard and the salt of deuterium labeled phosphoramide mustard which was not entrapped by liposomes by intravenous injection. The results are shown in Tables 7 and 8, and the corresponding plasma concentration time profile are shown in FIGS. 6 and 7.

TABLE 7

Pharmacokinetics of the Salt of Phosphoramide Mustard in the Rat

| Time minutes | Liposome-PM ($\mu$M) | *Free PM ($\mu$M) | Total PM ($\mu$M) | Pmd$_4$ |
|---|---|---|---|---|
| 5 | 224.1 | 28.41 | 231.6 | 37.80 |
| 15 | 96.94 | 20.51 | 150.2 | 18.63 |
| 30 | 74.71 | 9.947 | 95.21 | 5.959 |
| 45 | 45.37 | 4.780 | 58.75 | 3.192 |
| 60 | 25.55 | 2.815 | 29.08 | 1.858 |
| 90 | 12.46 | | 13.77 | |
| 120 | 5.140 | | 4.971 | |
| 150 | 3.069 | | 2.414 | |
| 180 | 2.034 | | 1.537 | |
| 210 | 0.958 | | 1.002 | |
| 240 | 0.692 | | 0.718 | |
| 300 | 0.370 | | 0.398 | |
| 360 | —. | | 0.390 | |
| 420 | 0.180 | | 0.206 | |
| 480 | | | 0.176 | |

*The salt of phosphoramide mustard leaked from liposomes
PM - salt of phosphoramide mustard
Pmd$_4$ - deuterium labeled salt of phosphoramide mustard (not entrapped in liposomes
Rat Weight 363 g.
Dose of PM-d0 1.789 mg (base form), Dose of PM-d$_4$ 1.714 mg

TABLE 8

Pharmacokinetics of the Salt of Phosphoramide Mustard in the Rat

| Time minutes | Liposome-PM ($\mu$M) | *Free PM ($\mu$M) | Total PM ($\mu$M) | PM-d$_4$ |
|---|---|---|---|---|
| 5 | 225.1 | 24.30 | 280.0 | 57.39 |
| 15 | 130.4 | 12.29 | 152.2 | 20.04 |
| 30 | 84.10 | 8.671 | 100.1 | 3.549 |
| 45 | 57.90 | 3.957 | 58.98 | 2.510 |
| 60 | 31.55 | 3.459 | 28.19 | 0.510 |
| 90 | 10.72 | | 9.535 | 0.596 |
| 120 | 4.210 | | 4.678 | 0.142 |
| 150 | 1.950 | | 1.685 | 0.032 |
| 180 | 1.210 | | 0.839 | |
| 210 | 0.722 | | 0.499 | |
| 240 | 0.476 | | 0.385 | |
| 300 | 0.304 | | 0.229 | |

TABLE 8-continued

Pharmacokinetics of the Salt of
Phosphoramide Mustard in the Rat

| Time minutes | Liposome-PM ($\mu$M) | *Free PM ($\mu$M) | Total PM ($\mu$M) | PM-d$_4$ |
|---|---|---|---|---|
| 360 | 0.134 | — | | |
| 420 | 0.106 | | 0.157 | |
| 480 | 0.075 | | 0.141 | |

Free PM: PM that leaked from liposomes
Total PM: Non entrapped PM
Rat Weight 378 g.
Dose of PM-d0 1.889 mg (base form), Dose of PM-d4 1.723 mg As can be seen from FIGS. 6 and 7 and Tables 7 and 8, the peak plasma level of total phosphoramide mustard for liposomal phosphoramide mustard was nearly 4-fold higher than that for the free phosphoramide mustard after normalized to the dose ($R_{Co}$=3.6±1.5(SD), n=8). The liposomal phosphoramide mustard showed a 5-fold reduction in steady-state volume of distribution ($R_{Vdss}$=4.8±3.3(SD), n=8). Liposomal phosphoramide mustard displayed a reduced total drug clearance by about 8-fold ($R_{CL}$=7.9±2.0(SD), n=8). As a result, the area under the concentration time curve of liposomal phosphoramide mustard was 8-fold greater than that of free phosphoramide mustard. The marked change in pharmacokinetics of liposomal phosphoramide mustard results from the entrapment of the liposomal phosphoramide mustard into the aqueous space of liposomes. The combined dose of the free phosphoramide mustard with the blank liposomes showed similar pharmacokinetics to the free phosphoramide mustard. When liposomal phosphoramide mustard was compared with phosphoramide mustard derived from cyclophosphamide, a 12-fold higher in the mean area under the curve of phosphoramide mustard generated from liposomal phosphoramide mustard than that of phosphoramide mustard derived from cyclophosphamide was observed ($R_{AUC}$=11.7±1.5(SD), n=3), after normalized to the dose. Plasma levels of phosphoramide mustard following administration of liposomes containing the phosphoramide mustard represented mostly as the entrapped form over an 8 hour period. The area under the curve of liposome-associated phosphoramide mustard was found to be 76.5±7.6% (SDN=6) of that of total phosphoramide mustard. The area under the curve of leaked phosphoramide mustard was calculated to be only 14.7±5.6% (SD, n=6) of that of total phosphoramide mustard. There appeared to be nearly a 50% reduction in the urinary excretion of phosphoramide mustard administered as liposomal phosphoramide mustard when compared to that of free phosphoramide mustard, although the biliary excretion did not contribute significantly as a major route of elimination for the liposomal phosphoramide mustard.

The entrapment of the phosphoramide mustard in liposomes significantly improved the pharmacokinetics and thereby provides a therapeutic advantage as compared to the free salt of phosphoramide mustard or phosphoramide mustard derived from cyclophosphamide. In addition, the liposomes showed significant integrity of lipid by layer membranes, particularly in the rat plasma in vivo no toxicity was observed.

The liposomes of the present invention are useful in the study and research into cancer and cancer treatments. In addition, the tiposomes are also useful in the treatment of cancer in a patient. While the invention has been described as employing unilamellar liposomes, multilamellar liposomes are also suitable.

What we claim is:

1. A pharmaceutical composition comprising:

dichlorodiethyl phosphoramide drug selected from the group consisting of isophosphoramide mustard, cyclohexylamine salt of phosphoramide mustard or mixtures thereof, and liposomes comprising sphingomyelin and cholesterol;

wherein the dichlorodiethyl phosphoramide drug is entrapped within the liposome.

2. The composition of claim 1, wherein the dichlorodiethyl phosphoramide is the cyclohexylamine salt of phosphoramide mustard.

3. The composition of claim 1, wherein the dichlorodiethyl phosphoramide is isophosphoramide mustard.

4. The composition of claim 1, wherein the sphingomyelin is bovine brain sphingomyelin.

5. The composition of claim 2, wherein the ratio of sphingomyelin to cholesterol is from about 2 to 1 to about 1 to 1.

6. The composition of claim 3, wherein the ratio of sphingomyelin to cholesterol is from about 2 to 1 to about 1 to 1.

7. The composition of claim 5, wherein the ratio of sphingomyelin to cholesterol is about 1 to 1.

8. The composition of claim 6, wherein the ratio of sphingomyelin to cholesterol is about 1 to 1.

9. A method for treating cancer in a patient comprising the steps of:

a. providing a dichlorodiethyl phosphoramide anti-cancer drug selected from the group consisting of isophosphoramide mustard, cyclohexylamine salt of phosphoramide mustard or mixtures thereof;

b. entrapping the drug of step (a) in liposomes; and c. administering an effective amount of the liposomes of step (b) to said cancer patient.

* * * * *